United States Patent
Herbst

(10) Patent No.: US 8,213,756 B2
(45) Date of Patent: Jul. 3, 2012

(54) BREATHABLE DOWNHOLE FIBER OPTIC CABLE AND A METHOD OF RESTORING PERFORMANCE

(75) Inventor: Brian Herbst, Easley, SC (US)

(73) Assignee: AFL Telecommunications LLC, Spartanburg, SC (US)

( * ) Notice: Subject to any disclaimer, the term of this patent is extended or adjusted under 35 U.S.C. 154(b) by 330 days.

(21) Appl. No.: 12/307,665

(22) PCT Filed: Oct. 23, 2007

(86) PCT No.: PCT/US2007/082174
§ 371 (c)(1),
(2), (4) Date: Jan. 6, 2009

(87) PCT Pub. No.: WO2008/051945
PCT Pub. Date: May 2, 2008

(65) Prior Publication Data
US 2010/0008632 A1    Jan. 14, 2010

Related U.S. Application Data

(60) Provisional application No. 60/862,666, filed on Oct. 24, 2006.

(51) Int. Cl.
*G02B 6/44* (2006.01)
(52) U.S. Cl. .......................... 385/109; 385/12; 385/100
(58) Field of Classification Search .................. None
See application file for complete search history.

(56) References Cited

U.S. PATENT DOCUMENTS

| | | | |
|---|---|---|---|
| 4,534,424 A | 8/1985 | Ramsey | |
| 4,697,453 A | 10/1987 | Murakawa et al. | |
| 4,772,128 A | 9/1988 | Vinarub et al. | |
| 4,944,570 A | 7/1990 | Oglesby et al. | |
| 6,557,630 B2 | 5/2003 | Harkins et al. | |
| 6,658,186 B1 * | 12/2003 | Kristensen et al. | 385/110 |
| 2003/0094281 A1 | 5/2003 | Tubel | |

FOREIGN PATENT DOCUMENTS

| | | |
|---|---|---|
| GB | 2 144 879 A | 3/1985 |
| GB | 2 159 978 A | 12/1985 |
| GB | 2 424 962 A | 10/2006 |
| JP | 05-157951 A | 6/1993 |
| JP | 05273446 A * | 10/1993 |

OTHER PUBLICATIONS

Russian Office Action of Mar. 19, 2010 issued in Russian Patent Application No. 2008147382/28(062037) (PCT/US2007/082174) with English translation.
European Search Report on Aug. 4, 2010.

* cited by examiner

*Primary Examiner* — Hemang Sanghavi
(74) *Attorney, Agent, or Firm* — Sughrue Mion, PLLC

(57) ABSTRACT

A breathable downhole fiber optic cable is provided having an outer protective tube; a fiber optic tube having a plurality of optical fibers contained therein; at least one annulus disposed between the outer protective tube and the fiber optic tube; and at least one path, extending through the length of the fiber optic cable, which provides a channel for a purge gas to flow for removing a second gas, such as hydrogen, from the fiber optic cable.

14 Claims, 8 Drawing Sheets

BREATHABLE DOWNHOLE FIBER OPTIC CABLE AND A METHOD OF RESTORING PERFORMANCE

CROSS-REFERENCE TO RELATED APPLICATIONS

This application claims priority from U.S. Provisional Application No. 60/862,666, filed on Oct. 24, 2006, the disclosure of which is incorporated herein by reference in its entirety.

BACKGROUND OF THE INVENTION

1. Field of the Invention

The present invention generally relates to fiber optic cables, and more particularly, relates to a breathable fiber optic cable which is ventilated to reduce hydrogen partial pressure next to the fiber.

2. Description of the Related Art

Fiber optic cables used for oil well applications where the cable is installed in the well have been problematic. One of the key concerns has been hydrogen darkening of the fiber. In the downhole environment, there is often free hydrogen present. Hydrogen can easily permeate the materials of the cable and diffuse into the optical fiber. The presence of hydrogen in the fiber will create an increase in transmission loss. This can make the systems that use the fiber—fiber optic pressure sensors and distributed temperature sensing—difficult if not impossible depending on the optical loss level in the fiber. Due to these issues, the cable structures used will often use hydrogen getters of various sorts to consume the present hydrogen. Other designs that resist hydrogen will include the use of a carbon layer on the optical fiber which will slow the diffusion of hydrogen into the glass. Unfortunately, some of the hydrogen getters are not suitable for temperatures above 150° C. and at higher temperatures are suspected of actually releasing the hydrogen they have captured. The use of a carbon layer has shown to lose its effectiveness as temperatures rise. Another feature used to improve the survivability in regard to hydrogen is to use additional metal layers in the cable that slow the diffusion of hydrogen. Metals such as copper, gold or aluminum are particularly good in slowing hydrogen diffusion. Manufacturers like FiberGuide and Oxford Electronics offer metal coated fibers. Unfortunately, although these options extend the life of the cable, these cable structures will show increased optical loss over time in the presence of hydrogen.

For example, one fiber optic cable uses a pure silica core fiber in cable structures designed for temperatures around 150° C. The purpose of this type of fiber is that the hydrogen, although it will still diffuse into the core of the fiber, will not react with dopants as the pure silica fiber does not have any in its core. Dopants such as germanium, fluoride and phosphorous are commonly used by fiber manufacturers to improve various attributes of the fiber. This is discussed in detail in "Development of Fibers Optic Cables for Permanent Geothermal Wellbore Deployment", R. Normann, J Weiss and J. Krumhansl. The issue with this logic is that diffusion rates of hydrogen in a pure silica fiber or a doped fiber is the same, so in the presence of the same hydrogen concentration both fiber types will exhibit attenuation loss. Although, the pure silica core will perform better as the loss associated with reactions with dopants is greater than the loss associated with hydrogen dispersed in the interstices of the glass core of the optical fiber. The loss associated with reactions to dopants has been documented at 100° C. and is documented in a white paper written by Joshua Jacobs titled "The Impact of Hydrogen on Optical Fibers".

Thus, the problem of survivability of fiber optic downhole cables has been approached with the intent of extending the life of the cable by creating barriers for the hydrogen. Inevitably, however, the hydrogen will get to the core of the fiber, especially at elevated temperatures.

SUMMARY OF THE INVENTION

Exemplary embodiments of the present invention overcome the above disadvantages and other disadvantages not described above. Also, the present invention is not required to overcome the disadvantages described above, and an exemplary embodiment of the present invention may not overcome any of the problems described above. The present invention provides a fiber optic cable structure which can breathe or ventilate to reduce hydrogen partial pressure next to the core of the fiber and a method of restoring performance in a fiber optic cable.

According to an exemplary embodiment of the present invention, there is provided a fiber optic cable apparatus, including an outer protective tube; a fiber optic tube having a plurality of optical fibers contained therein; at least one annulus disposed between the outer protective tube and the fiber optic tube; and at least one path, extending through the length of the fiber optic cable, which provides a channel for a purge gas to flow for removing hydrogen gas from the fiber optic cable.

In one alternative of the exemplary embodiment, the purge gas passes through a path and exits the path at the bottom of the fiber optic cable. The fiber optic cable may also be provided with an empty tube which extends through the length of the fiber optic cable. The path may be provided by any of the fiber optic tube, the empty tube or an annulus.

In another alternative of the exemplary embodiment, two paths may be provided. A first path may provide a first channel for the purge gas to flow down the fiber optic cable, and a second path may provide a second channel for the purge gas to return up the cable. A path connector connects the first path and the second path together at the bottom end of the cable, such that if the purge gas is injected into the fiber optic cable through the first path, the purge gas is returned through the second path via path connector. The first path and the second path may be provided by any of the fiber optic tube, the empty tube and an annulus, with the proviso that the first path and the second path do not occupy the same channel.

In addition, the fiber optic cable may include a barrier layer, made of carbon or metal (e.g., aluminum, gold or copper), disposed between two annuli. Either annulus may provide a channel for the first and second path, with the proviso that the first path and the second path do not occupy the same channel.

The purge gas may also flow through two paths via two separate channels in the same direction. For example, the purge gas can flow through the two annuli toward the bottom end of the cable.

According to another exemplary embodiment of the present invention, there is provided a method of restoring performance in a fiber optic cable, including providing a fiber optic cable having at least one path, extending through the length of the fiber optic cable, which provides a channel for a purge gas to flow for removing hydrogen gas from the fiber optic cable; and injecting a purge gas into the at least one path, wherein the hydrogen gas diffuses out of each of a plurality of optical fibers contained within the fiber optic cable.

The method of restoring performance in the fiber optic cable may also include monitoring the optical attenuation of the plurality of optical fibers and/or monitoring a return purge gas for hydrogen. In one alternative, the monitoring may include determining a level of optical attenuation in the plurality of optical fibers from monitoring levels of hydrogen within the return purge gas; and injecting the purge gas into the first path if the level of optical attenuation exceeds a predetermined threshold. In another alternative, the monitoring may include measuring the attenuation of the plurality of optical fibers by signal analysis; determining a time when a level of optical attenuation in the plurality of optical fibers will exceed a predetermined threshold; and injecting automatically the purge gas into the first path at the determined time.

Barriers and hydrogen getters can be combined with this invention to provide further improvements.

Accordingly, the fiber optic cable apparatus may include a barrier layer disposed on the outer surface of the optical fiber. For example, a carbon layer may be utilized on the fiber in this embodiment. Alternatively, a metal layer, such as copper, gold or aluminum, may be utilized.

Furthermore, the fiber optic cable apparatus may include a hydrogen getter, which captures hydrogen gas which has diffused into the optical fiber.

The advantage of the proposed structure/system is that the optical fibers attenuation will not be permanently degraded in this structure. Although it may increase, the purge process will restore the performance.

BRIEF DESCRIPTION OF THE DRAWINGS

The above and other aspects of the present invention will become more apparent from the following description of exemplary embodiments, taken in conjunction with the accompanying drawings of which.

Throughout the drawings, the same drawing reference numerals will be understood to refer to the same elements, features, and structures.

DETAILED DESCRIPTION OF THE EXEMPLARY EMBODIMENTS

The matters defined in the description such as a detailed construction and elements are provided to assist in a comprehensive understanding of the embodiment of the invention and are merely exemplary. Accordingly, those of ordinary skill in the art will recognize that various changes and modifications of the embodiment described herein can be made without departing from the scope and spirit of the invention. Also, descriptions of well-known functions and constructions are omitted for clarity and conciseness.

Figure 1:
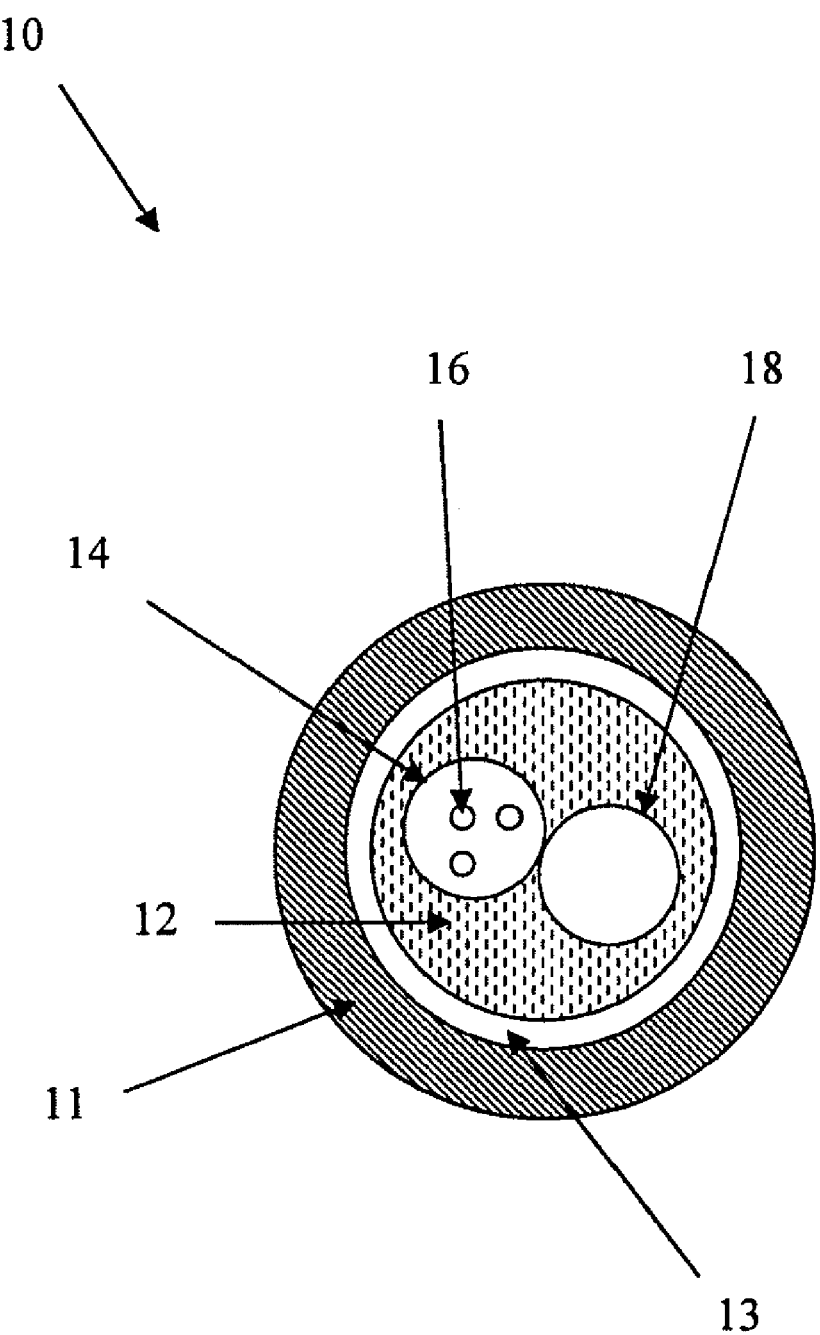
FIG. 1 illustrates a cross-sectional view of a fiber optic cable according to an exemplary embodiment of the present invention.

FIG. 1 illustrates a cross-sectional view of a fiber optic cable according to an exemplary embodiment of the present invention.

A fiber optic cable 10 is provided with an outer protective tube 11, a plastic extrusion 12, and an annulus 13 therebetween. Disposed within the plastic extrusion 12, there is provided a fiber optic tube 14 having a plurality of optical fibers 16 therein and an empty tube 18. At least one path, extending through the length of the fiber optic cable 10, provides a channel for a purge gas to flow for removing hydrogen gas from the fiber optic cable. Any one of the annulus 13, the fiber optic tube 14 and the empty tube 18 may provide a path for the purge gas to flow.

The outer protective tube 11 may be made of metal, such as stainless steel, Incoloy 825 or other. In addition, the outer shell of fiber optic tube 14 may be made of either stainless steel or plastic. Furthermore, the fiber optic tube 14 is filled with optical fibers, and may be a dry tube (i.e., without gel) or filled with gel.

When utilizing a purge gas to remove hydrogen gas from the core of the fiber optic cable 10, there may be provided a single path or a dual path.

Figure 7:
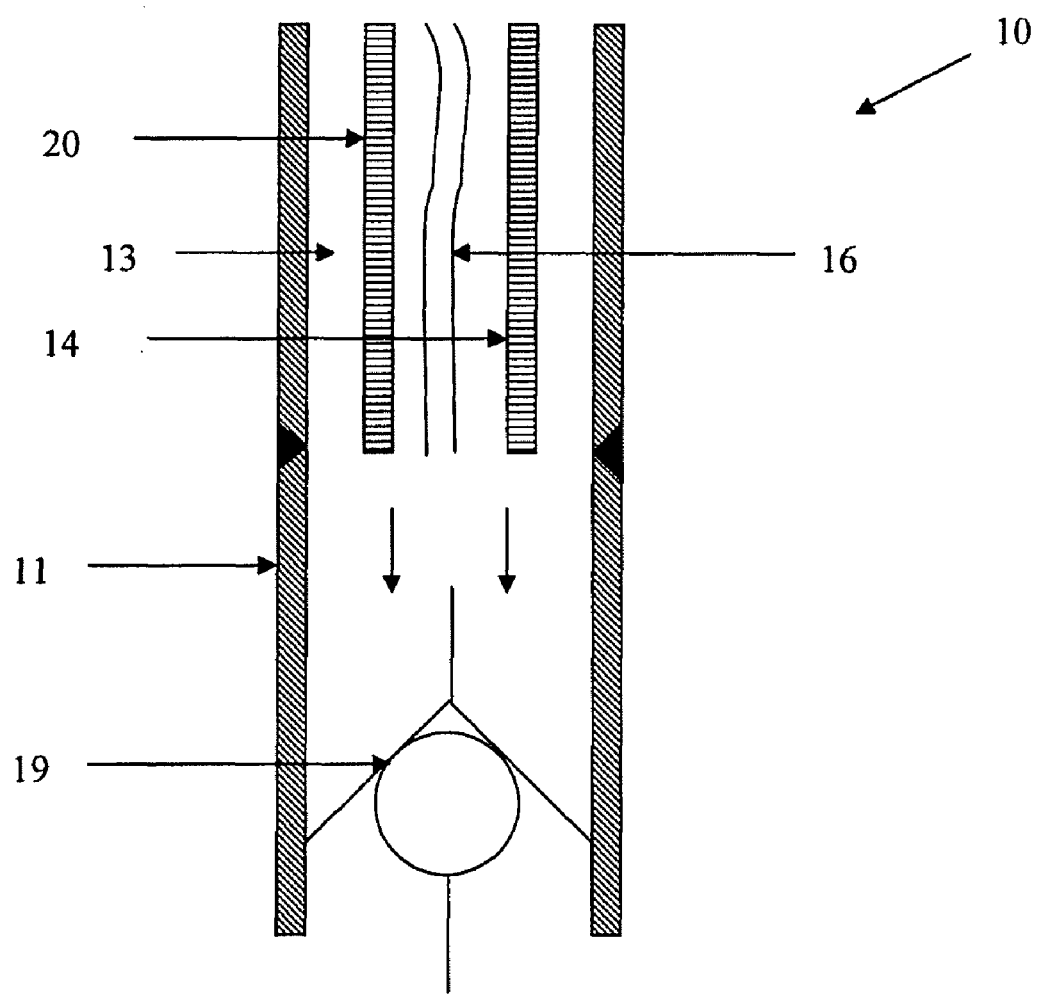
FIG. 7 illustrates a cross-sectional view of a bottom end of a fiber optic cable according to an exemplary embodiment of the present invention.

In regard to a single path, the purge gas may be injected to flow down the annulus 13, the fiber optic tube 14 and/or the empty tube 18. The purge gas passes through the path and exits the path at the bottom of the fiber optic cable 10. In this instance, a check valve system 19 (as illustrated in FIG. 7) is disposed at the bottom end of the fiber optic cable permitting the purge gas to exit the path. The check valve system 19 is used to help overcome the pressure in the well.

Figure 8:
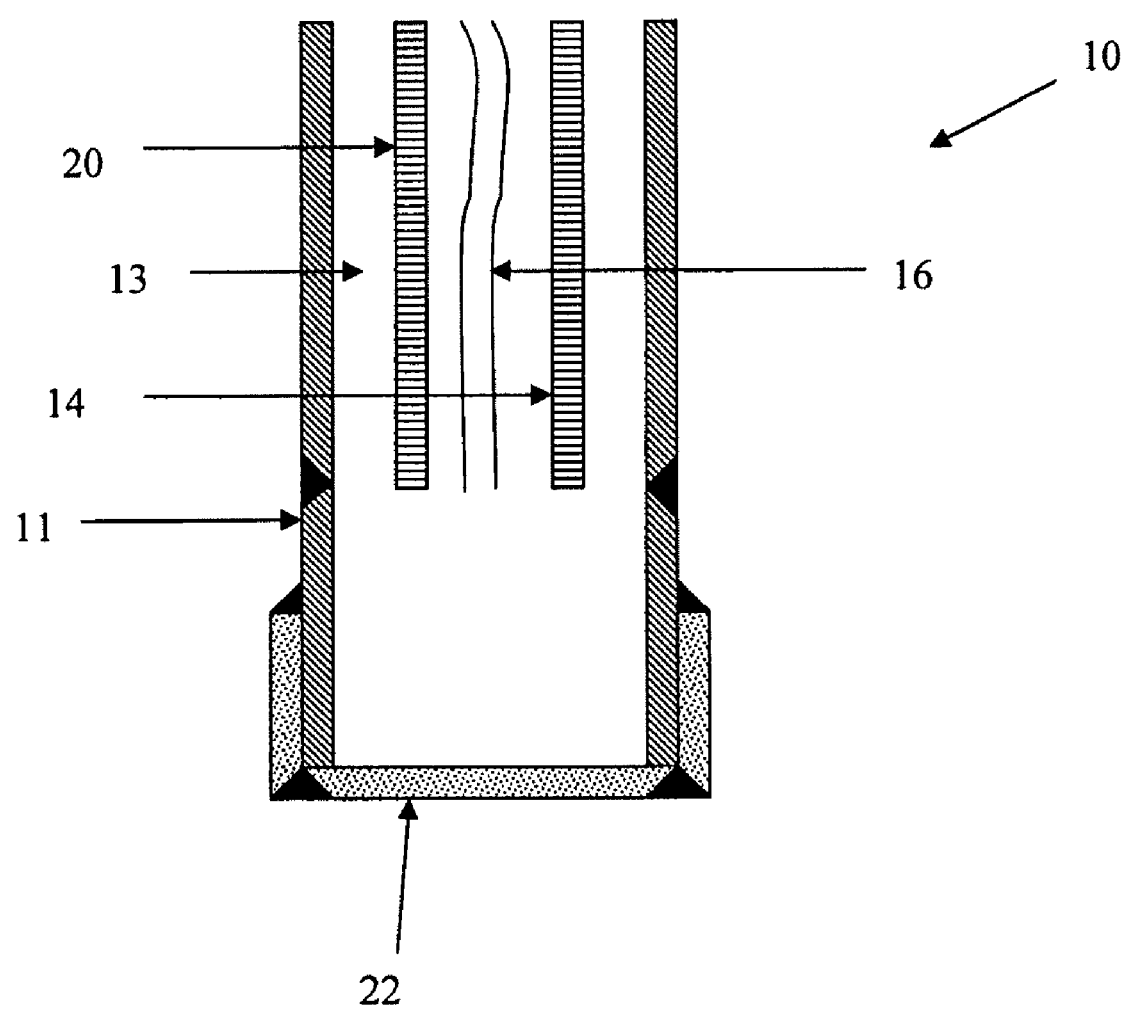
FIG. 8 illustrates a cross-sectional view of a bottom end of a fiber optic cable according to another exemplary embodiment of the present invention.

In regard to a dual path, the purge gas may be injected to flow down the fiber optic cable and to return back up the cable by separate paths. The downward path is connected to the upward path at the bottom end of the fiber optic cable 10 via a path connector. For example, the bottom end of the fiber optic cable 10 may be provided with an end cap 22 (as illustrated in FIG. 8) such that a pathway exists between the two paths such that the purge gas is forced to return by the second path as a result of the force of the injection of the purge gas by an injection pump, or the like. Alternatively, the two paths may be connected by a tube (not shown). Each path may be provided by either the annulus 13, the fiber optic tube 14 or the empty tube 18, with the proviso that the two paths do not occupy the same channel. For example, the purge gas may flow: (1) down the fiber optic tube 14 and up the empty tube 18; (2) down the fiber optic tube 14 and up the annulus 13; (3) down the empty tube 18 and up the fiber optic tube 14; (4) down the empty tube 18 and up the annulus 18; (5) down the annulus 13 and up the empty tube 18; or (6) down the annulus 13 and up the fiber optic tube 14.

Figure 2:
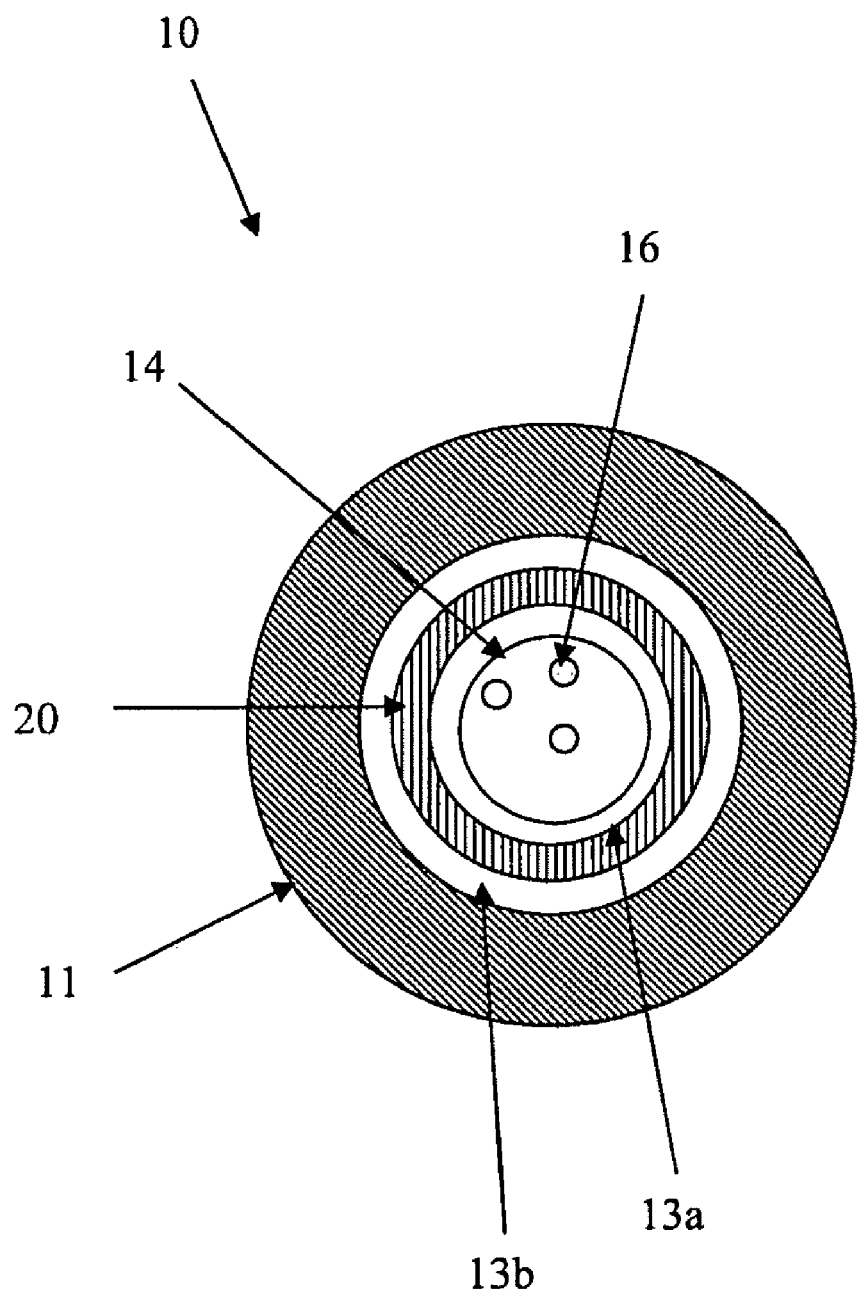
FIG. 2 illustrates a cross-sectional view of a fiber optic cable according to another exemplary embodiment of the present invention.

FIG. 2 illustrates a cross-sectional view of a fiber optic cable according to another exemplary embodiment of the present invention.

A fiber optic cable 10 includes a barrier layer 20, made of carbon or metal (e.g., aluminum, gold or copper), and disposed between a first annulus 13a and a second annulus 13b. The first annulus 13a, the barrier layer 20 and the second annulus 13b lie between an outer protective layer 11 and a fiber optic tube 14. Any one of the first annulus 13a, the second annulus 13b, and the fiber optic tube 14 may provide a path for the purge gas to flow, extending the length of the fiber optic cable 10.

Similar to that described in conjunction with FIG. 1, there may be provided a single path or a dual path for removing hydrogen gas with a purge gas.

In regard to the single path, the purge gas may be injected to flow down the first annulus 13a, the second annulus 13b and/or the fiber optic tube 14.

In regard to the dual path, each path may be provided by either the first annulus 13a, the second annulus 13b or the fiber optic tube 14, with the proviso that the two paths do not occupy the same channel. For example, the purge gas may flow: (1) down the fiber optic tube 14 and up the first annulus 13a; (2) down the fiber optic tube 14 and up the second annulus 13b; (3) down the first annulus 13a and up the fiber optic tube 14; (4) down the first annulus 13a and up the second annulus 13b; (5) down the second annulus 13b and up the first annulus 13a; and (6) down the second annulus 13b and up the fiber optic tube 14.

Figure 3:
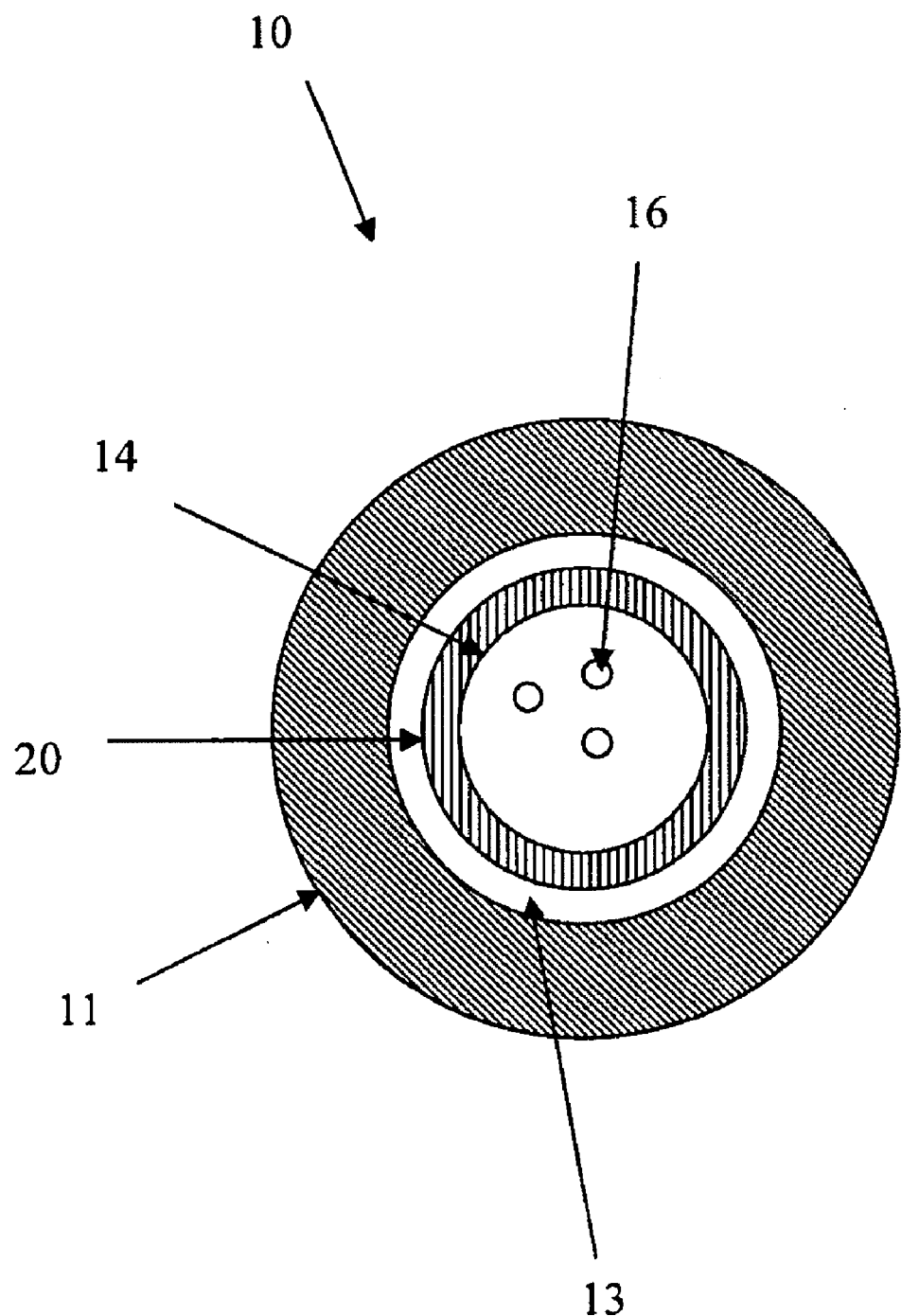
FIG. 3 illustrates a cross-sectional view of a fiber optic cable according to another exemplary embodiment of the present invention.

FIG. 3 illustrates a cross-sectional view of a fiber optic cable according to another exemplary embodiment of the present invention.

A fiber optic cable 10 includes a barrier layer 20 disposed on the outer surface of a fiber optic tube 14. The fiber optic cable 10 also includes an outer protective layer 11 and an annulus 13 between the outer protective layer 11 and the barrier layer 20. Any one of the annulus 13 and the fiber optic tube 14 may provide a path for the purge gas to flow, extending the length of the fiber optic cable 10.

Similar to that described in conjunction with FIG. 1, there may be provided a single path or a dual path for removing hydrogen gas with a purge gas.

In regard to the single path, the purge gas may be injected to flow down the annulus 13 and/or the fiber optic tube 14 (see FIG. 7).

In regard to the dual path, each path may be provided by either the annulus 13 or the fiber optic tube 14, with the proviso that the two paths do not occupy the same channel. For example, the purge gas may flow: (1) down the fiber optic tube 14 and up the annulus 13; and (2) down the annulus 13 and up the fiber optic tube 14 (see FIG. 8).

In addition, the fiber type is selected such as to ensure the hydrogen can diffuse out of the optical fiber, thus restoring the performance of the fiber. Furthermore, for low temperatures (e.g., 0-100° C.), a standard optical fiber with dopants may be used but as the temperature increases (e.g., greater than 100° C.), a pure silica fiber should be used. Moreover, a coating of the optical fiber should be used which can withstand the temperature. For example, a coating, such as polyimide, may be used to withstand temperatures upwards near 300° C.

In addition to the barrier layer 20 provided above, hydrogen getters (not shown) can be combined (alternatively or in addition thereto) with the present invention to provide further improvements. For example, hydrogen getters may be added to capture hydrogen gas which has diffused into the fiber optic cable 10.

In view of the foregoing, the intent is to deploy the fiber optic cable 10 and begin using the optical fiber as normal. If the attenuation begins to degrade, then a purge gas can be pushed through the cable structure. The structure can be such that the purge gas can pass through the cable 10 and exit at the bottom of the well at the end of the cable. This requires a check valve system 19 at the bottom and a high pressure of gas to overcome the pressure in the well. Alternatively, the purge gas has one path to go down the cable 10, a means to connect to a second path that extends up the cable 10. This allows for lower pressure and eliminates the need for a check valve system at the bottom of the well. The added benefit of this structure is that the return purge gas can be monitored for hydrogen. This allows the user to monitor the hydrogen reduction during the purge process. This characterization can be used to proactively purge the system periodically to keep the performance of the fiber within required specifications.

The advantage of the proposed structure/system is that the optical fibers attenuation will not be permanently degraded in this structure. Although it may increase, the purge process will restore the performance.

Figure 4:
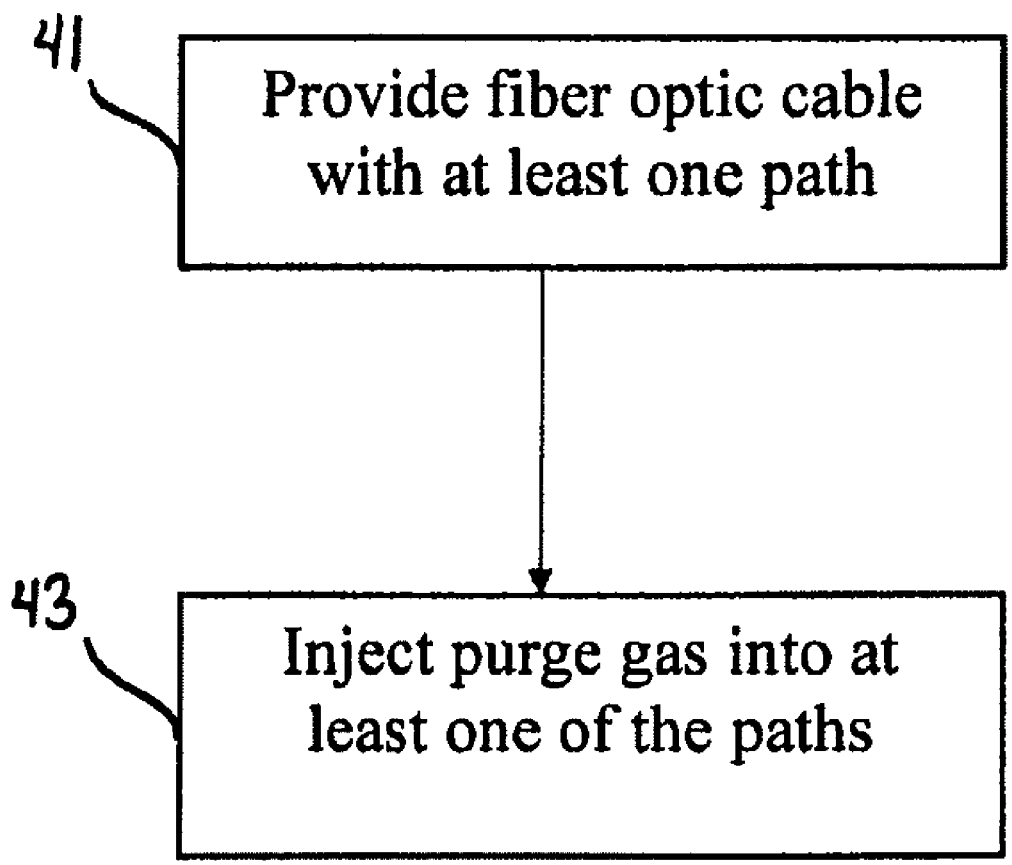
FIG. 4 illustrates a method for restoring performance in a fiber optic cable according to an exemplary embodiment of the present invention.

FIG. 4 illustrates a method for restoring performance in a fiber optic cable according to an exemplary embodiment of the present invention.

The method for restoring the performance includes providing a fiber optic cable 10 having at least one path (operation 41) and injecting a purge gas into the at least one path (operation 43). The path provides a channel for a purge gas to flow, which removes hydrogen gas from the fiber optic cable 10. When the purge gas is injected into one of the paths provided the hydrogen gas diffuses out of each of a plurality of optical fibers 16 contained within the fiber optic cable 10.

Figure 5:
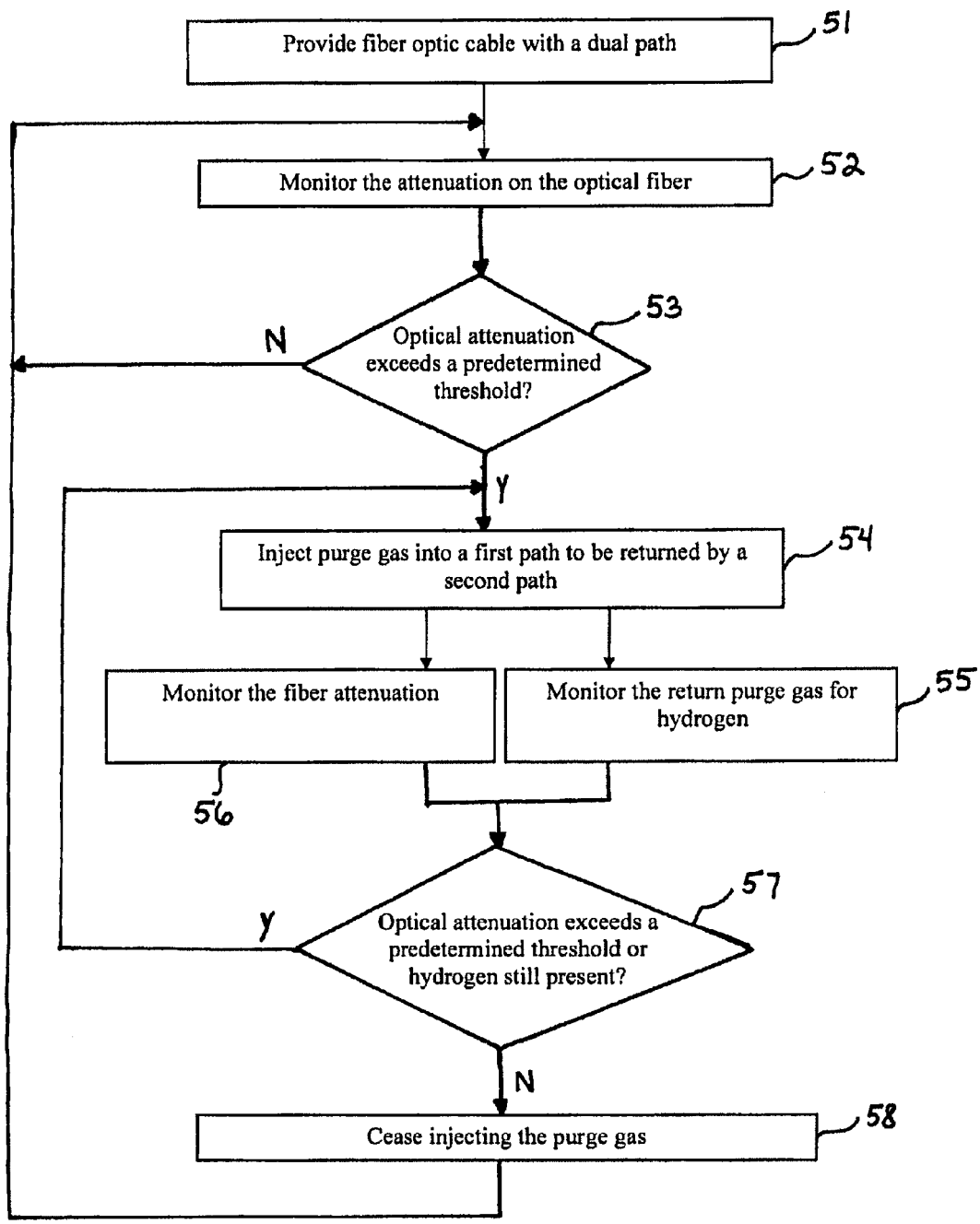
FIG. 5 illustrates a method for monitoring the performance in a fiber optic cable according to an exemplary embodiment of the present invention.

FIG. 5 illustrates a method monitoring the performance in a fiber optic cable according to an exemplary embodiment of the present invention.

The method for monitoring the performance in the fiber optic cable 10 includes providing a fiber optic cable 10 with a dual path (operation 51). The optical attenuation of the optical fiber is then monitored for an increase in optical loss (operation 52). Once the optical loss increases to a point determined by the user (operation 53), a purge gas is injected into one of the paths to be returned by the second path (operation 54), and the return purge gas can be monitored for hydrogen (operation 55). In addition, the attenuation in the optical fiber can also be monitored (operation 56). That is, the user can either use information on the hydrogen concentration or on the attenuation to determine the best time to cease the purge operation. If the optical attenuation exceeds a predetermined threshold or if hydrogen is still present in the fiber optic cable, then the injection of the purge gas continues via operation 54 (operation 57). On the other hand, if the optical attenuation returns to an acceptable level determined by the user or if is determined that no hydrogen is present, the purge process is ceased in operation 58. The acceptable level is determined by the user in accordance with the purpose and needs of the user. That is, the acceptable level may vary from site to site depending on the depth of the well and the equipment used, for example, in addition to the specific job the user is performing with the fiber optic cable. As the optical attenuation increases, the cycle starts again.

Figure 6:
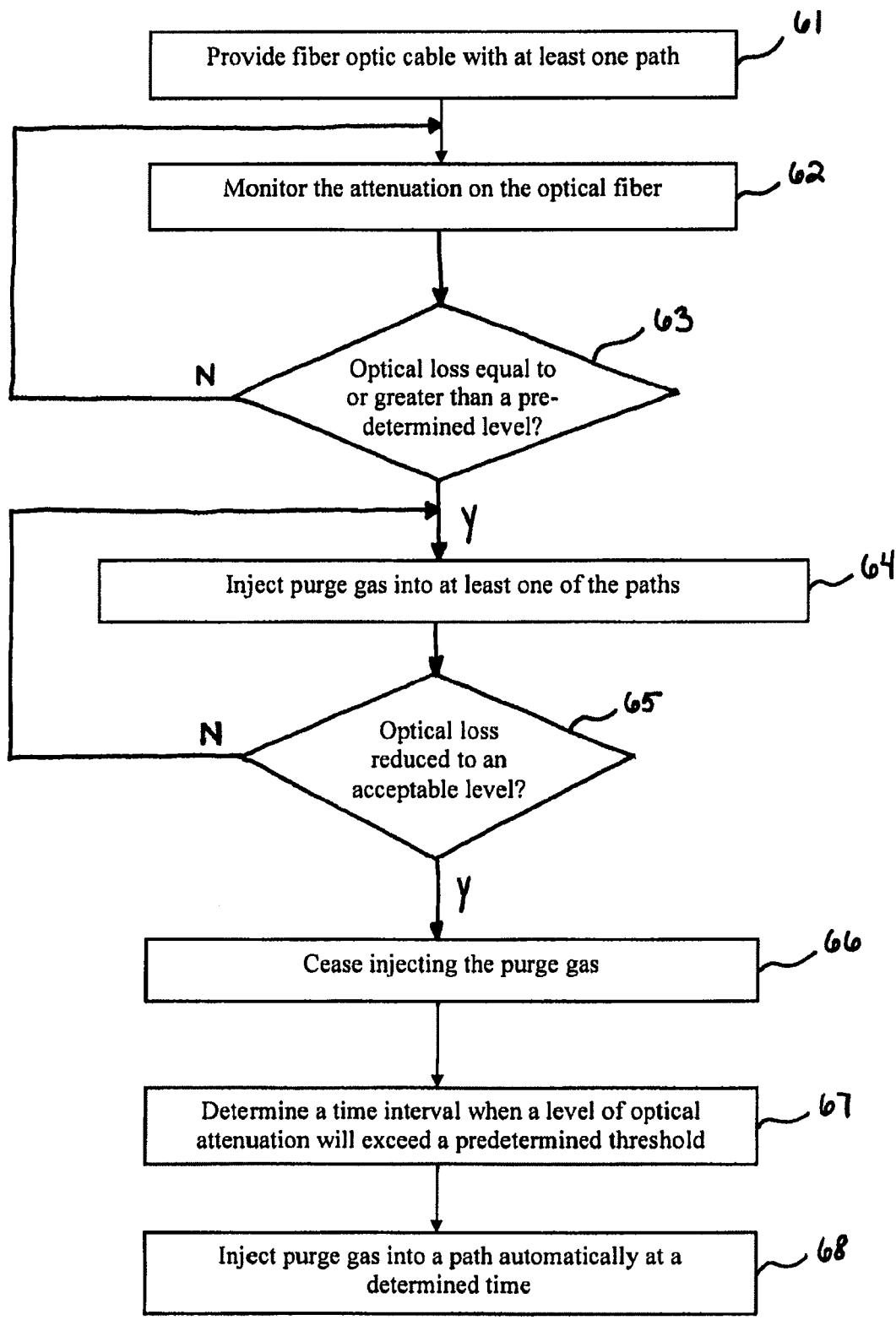
FIG. 6 illustrates a method for monitoring the performance in a fiber optic cable according to another exemplary embodiment of the present invention.

FIG. 6 illustrates a method for monitoring the performance in a fiber optic cable according to another exemplary embodiment of the present invention.

The method for monitoring the performance in the fiber optic cable 10 includes providing a fiber optic cable 10 with at least one path (operation 61), and monitoring the attenuation on the optical fibers (operation 62). Once the optical loss increases to a point determined by the user (operation 63), a purge gas is injected into at least one of the paths of the fiber optic cable (operation 64). Thereafter, it is determined whether the optical loss in the fiber optic cable has reduced to an acceptable level determined by the user (operation 65). If the optical loss has not returned to an acceptable level, the purge process continues via operation 64. Once the attenuation drops to an acceptable level, the purge process ceases in operation 66. The process begins again and as the user collects the time intervals between purge events, the user can, determine an expected time when a level of optical attenuation will exceed a predetermined threshold (operation 67), and automatically inject the purge gas into a path at the determined time (operation 68).

What is claimed is:

1. A fiber optic cable comprising:
an outer protective tube;
a fiber optic tube having a plurality of optical fibers contained therein;
at least one annulus disposed between the outer protective tube and the fiber optic tube;
a first path extending through the length of the fiber optic cable and which provides a first channel for a purge gas to flow in a first direction of the fiber optic cable, wherein the purge gas removes a second gas from the fiber optic cable;
a second path extending through the length of the fiber optic cable and which provides a second channel for the purge gas to flow in a second direction of the fiber optic cable, opposite the first direction; and
a means for connecting the first path to the second path,
wherein the purge gas is injected into the fiber optic cable through the first path and is returned through the second path via the means for connecting the first path to the second path, and
the returned purge gas is monitored by a monitoring unit for the second gas to determine whether the second gas is still present in the plurality of optical fibers, and if the second gas is still present, continuing the injection of the purge gas, and if the second gas is not present, ceasing the injection of the purge gas.

2. The fiber optic cable of claim 1, wherein:
the first path is provide by one of the fiber optic tube and a first annulus of the at least one annulus; and
the second path is provided by one of the fiber optic tube and the first annulus of the at least one annulus, wherein the first path and the second path do not occupy the same channel.

3. The fiber optic cable of claim 2, further comprises an empty tube which extends through the length of the fiber optic cable and provides a channel for the first path or the second path.

4. The fiber optic cable of claim 1, wherein the fiber optic cable further comprising a barrier layer disposed between a first annulus and a second annulus.

5. The fiber optic cable of claim 4, wherein:
the first path is provided by one of the fiber optic tube, the first annulus, and the second annulus; and
the second path is provided by one of the fiber optic tube, the first annulus, and the second annulus, wherein the first path and the second path do not occupy the same channel.

6. The fiber optic cable of claim 4, further comprising:
a third path which provides a third channel for the purge gas to flow in the first direction of the fiber optic cable,
wherein the first annulus provides the first path and the second annulus provides the third path.

7. The fiber optic cable of claim 4, wherein the barrier layer is a carbon layer or a metal layer.

8. A method of restoring performance in a fiber optic cable, the method comprising:
providing a fiber optic cable having at least one path, extending through the length of the fiber optic cable, which provides a channel for a purge gas to flow for removing a second gas from the fiber optic cable;
injecting a purge gas into the at least one path, wherein the second gas diffuses out of each of a plurality of optical fibers contained within the fiber optic cable;
determining a level of optical attenuation in the plurality of optical fibers; and
injecting the purge gas into the first path if the level of optical attenuation exceeds a predetermined threshold.

9. The method of claim 8, further comprising:
determining whether the level of optical attenuation in the plurality of optical fibers is reduced to an acceptable level; and
ceasing the injecting of the purge gas if the level of optical attenuation is determined to be at the acceptable level.

10. The method of claim 9, further comprising:
determining a time interval when the level of optical attenuation in the plurality of optical fibers will exceed the predetermined threshold by measuring the optical attenuation in the plurality of optical fibers; and
injecting automatically the purge gas into the at least one path at a determined time according to the determined time interval.

11. A method of restoring performance in a fiber optic cable, the method comprising:
providing a fiber optic cable having at least one path, extending through the length of the fiber optic cable, which provides a channel for a purge gas to flow for removing a second gas from the fiber optic cable;
injecting a purge gas into the at least one path, wherein the second gas diffuses out of each of a plurality of optical fibers contained within the fiber optic cable;
monitoring a return purge gas for the second gas;
determining whether the second gas is still present in the plurality of optical fibers, wherein if the second gas is still present, continuing the injection of the purge gas, and if the second gas is not present, ceasing the injection of the purge gas, and wherein the fiber optic cable includes:
a first path which provides a first channel for the purge gas to flow in a first direction of the fiber optic cable;
a second path which provides a second channel for the purge gas to flow in a second direction of the fiber optic cable, opposite the first direction; and
a means for connecting the first path to the second path,
wherein the purge gas is injected into the fiber optic cable through the first path and is returned through the second path via the means for connecting the first path to the second path.

12. The method of claim 11, wherein the determining whether the second gas is still present in the plurality of optical fibers includes correlating a level of optical attenuation in the plurality of optical fibers with a level of the second gas in the return purge gas.

13. The method of claim 12, further comprising injecting the purge gas into the at least one path if the level of optical attenuation exceeds a predetermined threshold.

14. The method of claim 12, wherein the second gas is hydrogen gas.

* * * * *